United States Patent [19]

Russell

[11] Patent Number: 6,050,931

[45] Date of Patent: Apr. 18, 2000

[54] MAGNETIC THERAPEUTIC DEVICE FOR ARTHRITIC FINGERS

[76] Inventor: John J. Russell, 17 Langley La., Old Westbury, N.Y. 11590

[21] Appl. No.: 08/880,771

[22] Filed: Jun. 23, 1997

[51] Int. Cl.[7] .................................................. A61N 1/00
[52] U.S. Cl. .................................................. 600/15
[58] Field of Search ........................................ 600/9–15

[56] References Cited

U.S. PATENT DOCUMENTS

| | | | |
|---|---|---|---|
| 5,137,507 | 8/1992 | Park | 600/13 |
| 5,707,333 | 1/1998 | Bakst | 600/15 |
| 5,720,046 | 2/1998 | Lopez et al. | 600/15 |
| 5,782,743 | 7/1998 | Russell | 600/15 |

*Primary Examiner*—John P. Lacyk

[57] ABSTRACT

Magnetic therapeutic device provides small lightweight rare-earth intense-field permanent magnets encased in a stretchable polymeric resin carrier held adjustably in position on the finger and joint areas of an arthritic hand by a resilient support strap attached to the ends of the magnet-carrier.

8 Claims, 3 Drawing Sheets

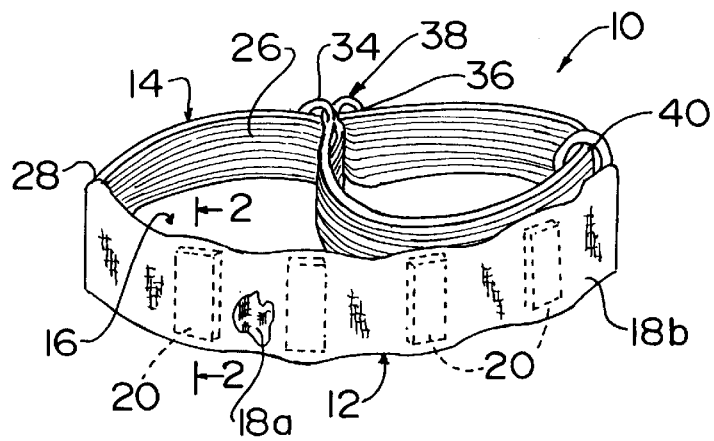
FIG. 1
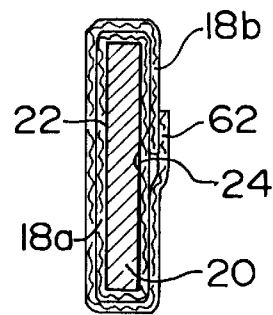
FIG. 2
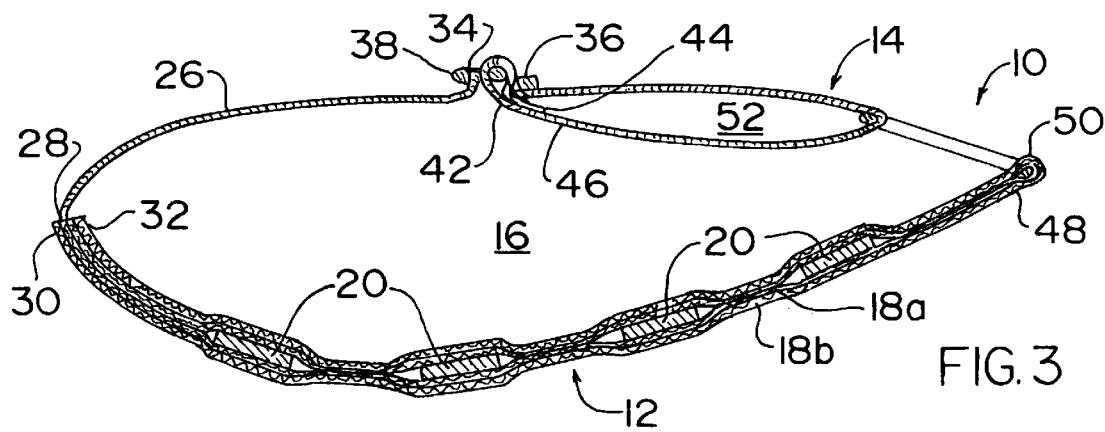
FIG. 3
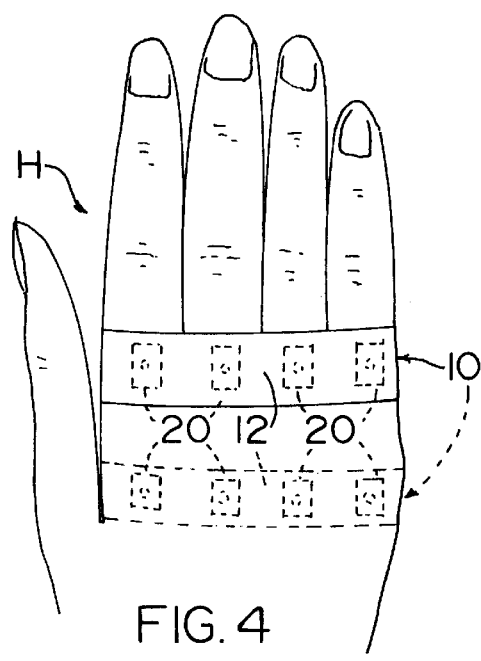
FIG. 4
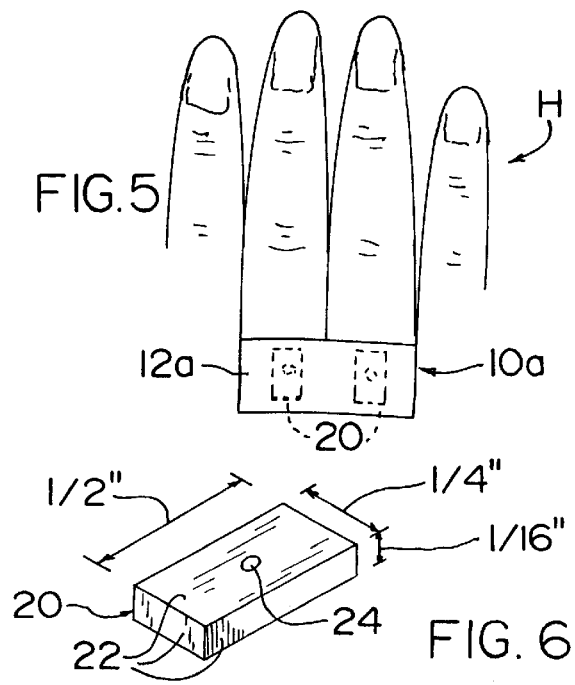
FIG. 5
FIG. 6

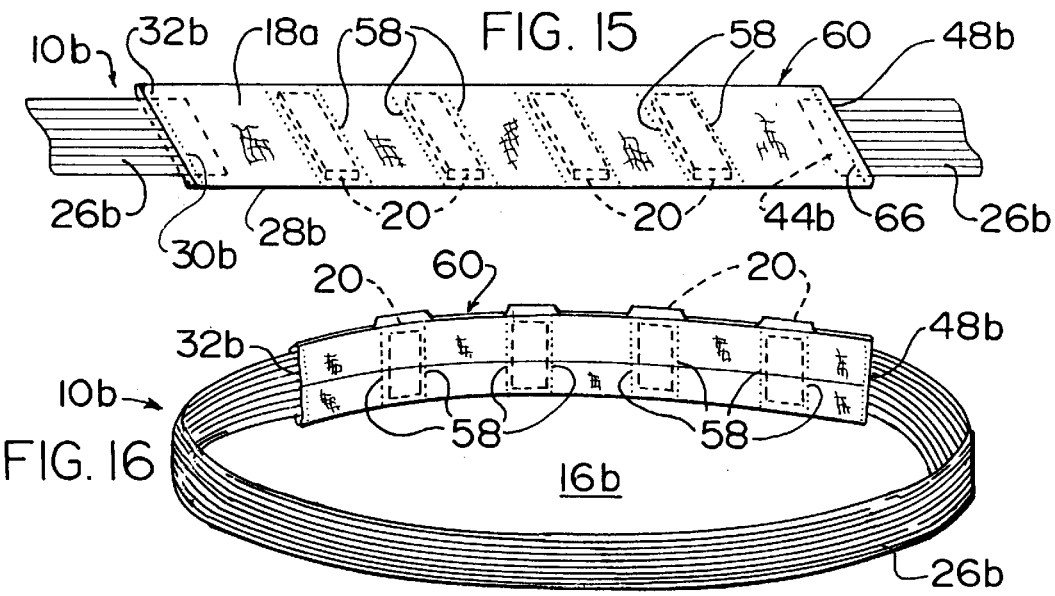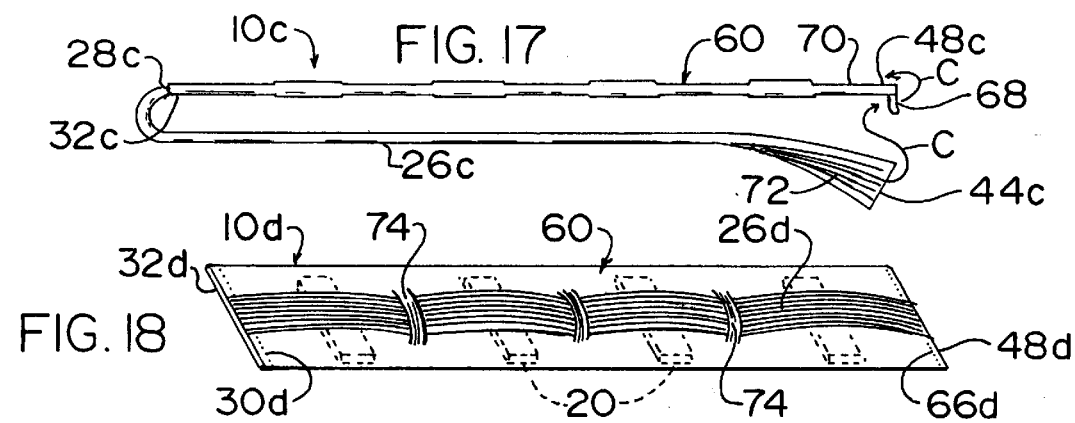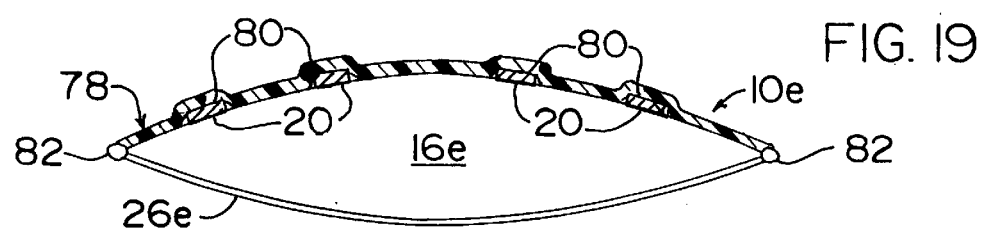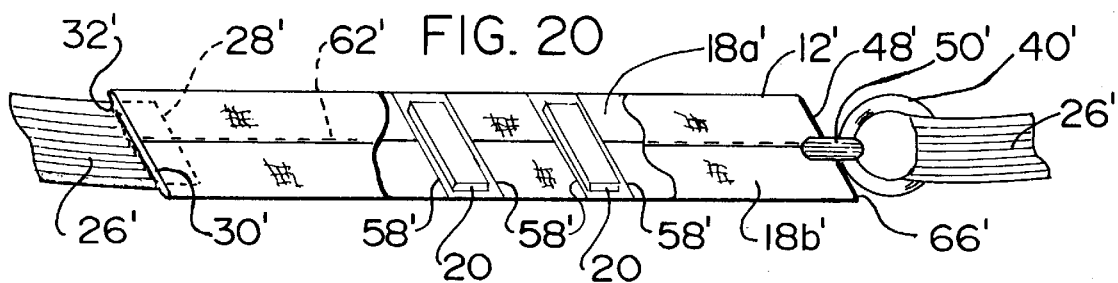

MAGNETIC THERAPEUTIC DEVICE FOR ARTHRITIC FINGERS

BACKGROUND OF THE INVENTION

A. Field of the Invention

This invention relates to devices for applying magnets adjustably to fingers of the hand of a user for therapeutic pain-easing and healing effects. More specifically, this invention is concerned with flexible stretchable fabric or polymeric resin bands with small thin powerful rare-earth magnets secured and positioned therein to be mounted selectively, adjustably, comfortably and removably on or near painful or stiff arthritic fingers for non-invasive effective treatment and symptomatic pain relief for the device's user.

B. Description of the Prior Art

In the treatment of the aching, soreness and stiffness of arthritic fingers and hands, the prior art has thus far provided little comfort or help. For temporary relief, the medical profession relies principally on the ingestion of pain-killing or anti-inflammatory drugs, or the injection of steroids, gold and the like; topical applications of analgesic creams or lotions and/or heat are sometimes recommended; and acupuncture has reportedly helped some patients. Heretofore, however, magnetic therapy for this purpose has been essentially unsuccessful due to the awkward motion-restricting character of bulky, heavy magnets encased in gloves or windings thus far available.

In general, the practice of using magnets for healing and the reduction of pain has been known for centuries and practiced all over the world. Magnets have proved to be the most natural, effective and economical means of treating pains and ailments of the body, without resorting to the use of drugs in the form of injections, pills and ointments, or in body-invasive procedures. It is well established that when applied to painful areas of the body, magnets deliver the energy of the magnetic flux field emanating therefrom to penetrate the user's body tissue and to energize, speed circulation of, and accelerate the oxygenation of the blood; as a result, moderate heat is generated, blood flow is increased, the pain is eased and the body is aided and encouraged to perform its natural healing functions.

It is therefore the primary object of this invention to apply the advantages of magnetic therapy to, and to provide a therapeutic magnet-containing device for placement on or near, the finger and joint areas of an arthritic hand. It is also the object of this invention to provide a device which is light in weight, adjustable in size, comfortable to wear, non-restrictive of motion of the hand on which it is worn and, above all, which effectively reduces arthritc pain, working toward reversing calcium deposition and restoring normal function of the fingers and hand.

SUMMARY OF THE INVENTION

The present invention provides a therapeutic device for holding a plurality of small lightweight intense-field permanent magnets on or near the finger and joint areas of an arthritic hand to reduce the pain, stiffness and soreness and to promote healing therein. The device comprises a number of flat powerful rare-earth magnets (generally one for each finger area being treated), each magnet being spacedly secured in a flexible carrier band for positioning the magnets on or near the fingers or joints being treated, on either the upper or palm side of the hand. The carrier band has an adjustable resilient strap attached to each end thereof, thus completing an elliptically-shaped device which can fittingly surround substantially any sized afflicted hand inserted therein.

Full details of the structures, features and uses of the preferred embodiments of this invention will be disclosed and described in connection with the accompanying illustrative but not limiting drawings, wherein:

BRIEF DESCRIPTION OF THE DRAWINGS

FIG. 1 is a front perspective view of a preferred embodiment of a magnet-carrying therapeutic device made in accordance with this invention;

FIG. 2 is a vertical sectional view taken along line 2—2 of FIG. 1;

FIG. 3 is a transverse sectional view taken through the therapeutic device shown in FIG. 1;

FIG. 4 is a plan view of a hand wearing the therapeutic device of FIG. 1 shown in two optional positions;

FIG. 5 is a partial plan view of a hand wearing another embodiment of the therapeutic device of this invention for selectively treating two fingers of the hand;

FIG. 6 is a top left perspective view of one of the small flat rare-earth magnets used in this invention;

FIG. 15 is a rear left perspective partial view of another embodiment of this invention;

FIG. 16 is a rear perspective view of the entire therapeutic device shown in FIG. 15;

FIG. 17 is an side view of another embodiment of this invention;

FIG. 18 is a left rear perspective view of still another embodiment of a therapeutic device practicing this invention;

FIG. 19 is a side view partially in section of yet another embodiment of a therapeutic device of this invention; and FIG. 20 is a left rear perspective partial view, partly broken away and similar to FIG. 14, showing a variant thereof.

DESCRIPTION OF THE PREFERRED EMBODIMENTS

Figure 7:
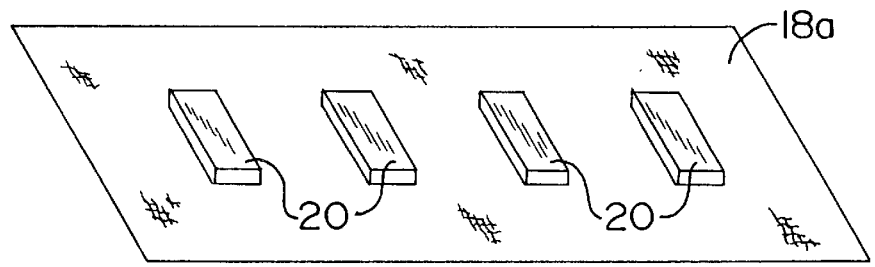
FIGS. 7–14 illustrate the method used in the assembly of the therapeutic device of FIG. 1, showing the successive steps taken.
Figure 8:
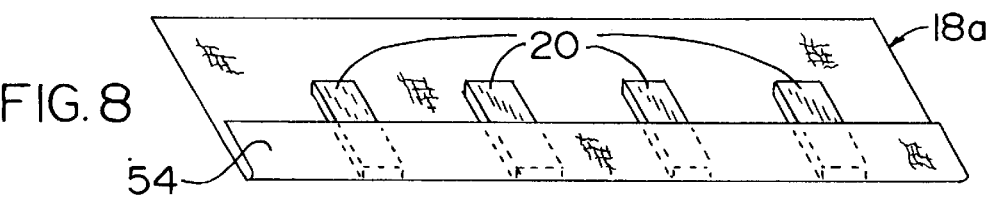

The preferred magnetic therapeutic device shown in FIGS. 1–4 and generally designated 10 comprises magnet-carrying member 12 having elasticized resilient length-adjustable strap assembly 14 attached to the ends thereof. Device 10, as best seen in FIG. 3, is generally elliptical in shape, forming opening 16 into which a user's fingers or hand may be fittingly placed to reach a selected position of treatment such as those shown in FIG. 4, or reversed so that member 12 and magnets 20 held therein are facing the palm side of the hand being treated.

Member 12 is formed from two layers of stretchable fabric 18a, 18a woven from synthetic polymer fibers; layers 18, 18a encase and hold four spaced high-energy rare-earth permanent magnets 20 in position so that each magnet 20 can send its flux field energy penetratingly into the corresponding finger and joint area of the hand wearing device 10. A preferred flesh-colored fabric for layers 18a, 18b is available and sold under the name "LYCRA", a registered trademark of E. I. Dupont de Nemours, Inc., Wilmington, Del.

The method of assembling magnet-carrying member 12 will be described fully hereinafter in connection with FIGS.

7–14. As seen in FIG. 6, each rectangular rare-earth magnet 20 is very thin (1/16"), very small in size (1/2"×1/4") and extremely lightweight (approximately 0.1 ounce). Despite their small mass, permanent magnets 20, made from the rare earth neodymium combined with iron boron ferrite, generate remarkably intense magnetic fields (for standardization purposes, each magnet 20 is rated at 12,500 gauss); each magnet 20 has gold plating 22 (see FIG. 2) to protect the skin of the user from irritation or allergic reaction and to protect each magnet 20 from corrosion. A centrally disposed small recess or "dimple" 24 appears on one side of each magnet 20 to identify the south pole thereof; for most magnetic therapy treatments, magnet 20's north pole normally is directed toward the area being treated, but reversing or even alternating the magnets– polarity may be used in some cases for possible improved treatment results.

FIGS. 1 and 3 show strap assembly 14 comprising resilient elasticized strap 26, end 28 of which is fastened by stitching 30 to end 32 of member 12. From end 28, strap 26 extends through slot openings 34, 36 of adjustment clip 38, on through resin polymer ring 40 and back around clip 38's center post 42, which separates slot openings 34, 36 and to which strap 26's opposite end 44 is rotatably secured to itself by stitching 46. Ring 40, in turn, is flexibly attached to member 12's opposite end 48 by loop stitching 50, finishing the joining of member 12 and strap assembly 14 to complete device 10 and to close hand-accepting space 16 formed thereby. Size adjustment of device 10 is readily accomplished by moving adjustment clip 38 in either direction along strap 26's length; in the position shown in FIG. 3, sliding clip 26 to the left will increase the size of secondary space 52 and decrease the size of space 16 so that device 10 will fit a smaller hand, while movement of clip 26 to the right in FIG. 3 will enlarge space 16 to accommodate a larger hand, giving device 10 a "one-fits-all" capacity.

In FIG. 4, device 10 is shown in two optional positions of use on hand H, the solid line location being between the fingers–second joints and the knuckles, the phantom line location beyond the knuckles and to the bottom of the V between thumb and forefinger; other locations on the fingers or hand may be used, and as previously noted (but not shown), device 10 may be positioned so that magnets 20 face the palm side of hand H as well.

Device 10a of FIG. 6 has magnet-carrying member 12a with two magnets 20 supported therein and is sized to be placed on, and to treat, two finger areas of hand H. Not shown but obviously contemplated is an analogous three-finger version of this invention; also not shown is the strap assembly means for device 10a, which may correspond to assembly 14 of FIG. 3, or to other embodiments of resilient elasticized strap means hereinafter disclosed.

Figure 9:
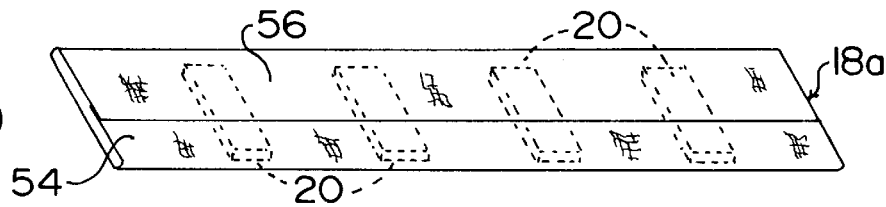

A preferred method of producing magnet-carrying element 12 is illustrated in FIGS. 7–14. In FIG. 7, a flat rectangular piece of stretchable fabric 18a woven from polymeric resinfibers has four rare-earth neodymium magnets 20 spacedly placed parallel to each other and transversely on fabric 18a, with the long axis of each magnet 20 perpendicular to the long axis of fabric piece 18a. Next, in FIG. 8, one side 54 of fabric 18a has been folded longitudinally to contact the adjacent ends of the aligned magnets 20 and to cover approximately half of the exposed upper surfaces thereof. FIG. 9 shows the opposite side 56 of fabric 18a folded longitudinally to be in contact with the aligned opposite ends of magnets 20 and to cover the remaining exposed magnet surfaces, slightly overlapping previously made fold 54. Sub-assembly 60 is then completed, as in FIG. 10, by creating transverse rows of stitches 58 closely adjacent and parallel to both sides of magnets 20; in this way, magnets 20 are each encpsulated, side folds 54, 56 are secured in place and sub-assembly 60 may be freely handled. Alternatively, stitches 68 may be replaced by heat-sealing fabric 18a together alongside each magnet 20 (see FIG. 20).

Figure 11:
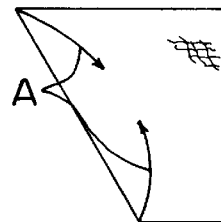
Figure 12:
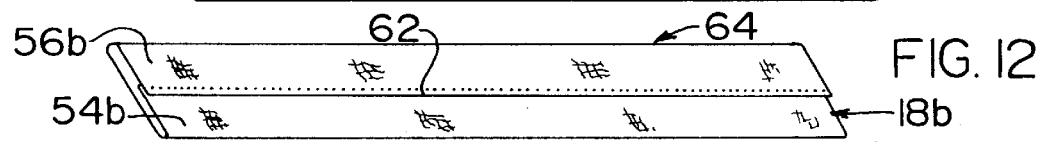
Figure 13:
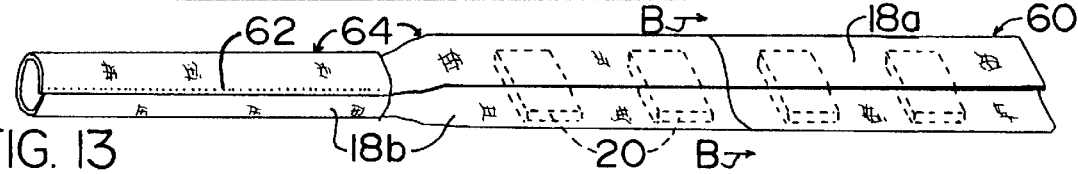
Figure 14:
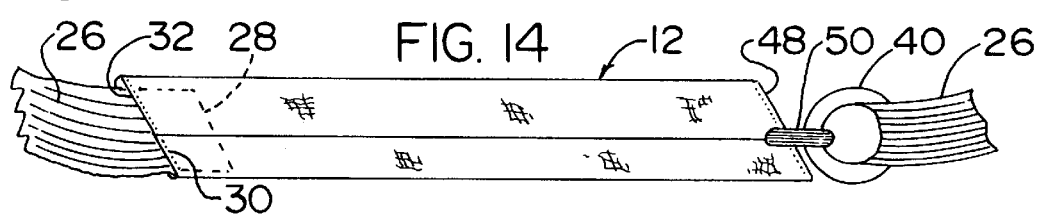

As seen in FIGS. 11 and 12, a second piece of stretchable fabric 18b, identical to fabric piece 18a, is folded longitudinally on both sides in the directions of arrows A to form parallel, slightly overlapping folds 54b and 56b, which are then sewn together by length-wise stitching 62, resulting in the formation of hollow fabric sheath or tube 64. Here again, heat-sealing may be used to substitute for stitching 62 (see FIG. 20 ). Where stitching 62 is used, sheath 64 is now turned inside-out and one end thereof is pulled in the direction of arrows B to be aligned with and to cover sub-assembly 60 (FIG. 13). Finally, in FIG. 14, the assembly of magnet-carrying member 12 and of device 10 is completed by: inserting end 28 of support strap 26 into the opening of end 32 of fabrics 18a, 18b and securing it thereto by transverse stitching 30 (or heat-sealing); by applying loop stitching 50 at the opposite end 48 of member 12 to secure ring 40 thereto flexibly; and by passing end 44 of strap 26 through ring 40, by looping it around center post 42 of clip 38, and by securing end 44 yhereto by stitching 46 (see FIG. 3).

Figure 10:
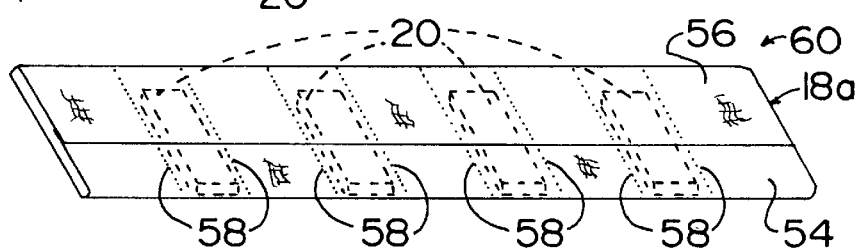

Another simplified embodiment of a therapeutic device 10b of this invention is illustrated in FIGS. 15 and 16, wherein sheath 64 of device 10 is eliminated, and sub-assembly 60 shown in FIG. 10 serves as the magnet-carrying member. Ends 28b and 44b of elasticized strap element 26b are attached respectively to ends 32b and 48b of sub-assembly 60 shown here by transverse stitching 30b and 66. Device 10b as shown relies on the elasticity of both elasticized strap element 26b and stretchable fabric 18a of sub-assembly 60 for automatic size adjustment. In a further modification of device 10b shown in FIG. 17, device 10c uses sub-assembly 60 with elasticized strap means 26c's end 28c attached at end 32c thereof, identically to device 10b; however, opposite end 48c of sub-assembly 60 carries loop 68 on its inner side and a piece of loop-type fabric 70 on its outer side, while end 44c of strap means 26c is covered on its inner face with hook-type fabric 72.The combination of fabrics 70 and 72 when pressed together after putting end 44c through loop 68 and folding end 44c over, as indicated by arrows C, serves as a size-adjusting fastening means; this combination of hook-type and loop-type fabrics is available and sold under the registered trademark "VELCRO". It is clear that hook- and loop-type fastening means may be incorporated into device 10b of FIGS. 15, 16, if desired, to accommodate hands of all sizes.

Therapeutic finger treating device 10d in FIG. 18 also uses sub-assembly 60 as its magnet-carrying member, but its elasticized strap means 26d is somewhat narrower in width than straps 26, 26a–c described above. Strap 26d is secured to sub-assembly 60 at its ends 32d and 48d by transverse stitching 38d and 66d respectively (or heat-sealed), and is restrained by three spaced transverse elasticized loops 74, the ends of which are stitched or sealed to the inner surface of sub-assembly 60. As a result, strap means 26d is divided to form four finger openings 76 which automatically adjust size and tension balance when the fingers to be treated are inserted therein and strap 26d slides in either direction under each loop 74.

Still another embodiment 10e is shown in FIG. 19; here, molded soft resilient polymeric resin shell 78 is the magnet-carrying member, with spaced molded sockets 80 provided to accommodate magnets 20 secured adhesively therein. Connecting loops 82 attached at each end of shell 78 are provided to connect elasticized strap means 26e thereto, thus forming space 16e for the insertion of fingers to be treated. As with the previously disclosed embodiments, strap means 26e may be replaced with alternate size-adjustment means described above.

FIG. 20 illustrates the substitution of heat-sealing for stitching. Here, magnet-carrying member 12' has magnets 20 ecapsulated by heat-sealed stripes 58' on fabric 18a', sheath 18b' held together by longitudinal heat seal 62', and resilient support strap 26' heat-sealed in place by stripe 30' at end 32' of member 12', opposite end of which 48' being heat-sealed by stripe 66' Loop 50' for flexibly holding ring 40' through which strap 26' passes completes magnetic therapeutic device 10'.

The various preferred embodiments of, and the best means of practicing, this invention now contemplated, have been fully disclosed and described. It will be evident to one skilled in the art that various substitutions, alternatives and modifications may be made without departing from the concepts of this invention, which are limited only by the scope of the ensuing claims, wherein:

What is claimed is:

1. Magnetic therapeutic device for the relief of arthritic pain and stiffness in a user's fingers and hand, which comprises:

a plurality of flat rectangular rare-earth high-energy permanent magnets, one said magnet for each finger area to be treated;

flexible means for carrying and holding said plurality of magnets in spaced position on the user's hand so that each of said plurality of magnets is substantially aligned with the hand's corresponding finger; and resilient support strap means for attachment of one of each end thereof to one of each end of said magnet-carrying means, whereby the substantially elliptical therapeutic device so formed defines a correspondingly shaped opening into which the user's fingers adapted to be projected inserted to mount the device transversely to, and fittingly on, the user's hand for therapeutic treatment.

2. Magnetic therapeutic device as defined in claim 1, wherein each one of said plurality of permanent magnets comprises a combination of rare-earth element neodymium and iron boron ferrite, and each said magnet is gold-plated to prevent corrosion of said magnet and adapted to avoid irritation or allergic reaction of a device user's skin.

3. Magnetic therapeutic device as defined in claim 1, wherein said magnet-carrying means is a molded elongate shell formed from soft flexible polymeric resin material, said elongate shell having a plurality of sockets spacedly positioned along the length of said shell, each of said sockets being dimensioned to accommodate fittingly one of said plurality of magnets adhesively mounted therein.

4. Magnetic therapeutic device as defined in claim 1, wherein said resilient support strap means comprises a suitable length of elasticized strap connecting the ends of said magnet-carrying means.

5. Magnetic therapeutic device as defined in claim 4, wherein said resilient support strap means further comprises at least one transverse elasticized loop, the ends of said at least one transverse loop being secured to an inner surface of said magnet-carrying means, said at least one transverse loop extending over and across said elasticized strap and said magnet-carrier means' inner surface to form at least two transverse looped openings therebetween, each said transverse looped opening being aligned with one of said plurality of magnets in said magnet-carrying means and being dimensioned to be adapted to permit the introduction of a finger fittingly therethrough for magnetic therapy treatment thereof.

6. Magnetic therapeutic device as defined in claim 4, wherein said resilient support strap means further comprises means for adjusting the effective length of said resilient support strap means, whereby the size of said elliptical opening in the magnetic therapeutic device is adapted to be selectively adjusted to fit any arthritic hand requiring treatment.

7. Magnetic therapeutic device as defined in claim 6, wherein said adjustment means comprises a combination of lengths of loop and hook fabrics, one mounted on one end of said elasticized strap, the other secured to an outer surface of said magnet-carrying means, whereby said loop and said hook fabric lengths are adapted to be selectively positioned laterally with respect to each other and joined to apply the magnetic therapeutic device fittingly to a user's hand.

8. Magnetic therapeutic device as defined in claim 6, wherein said adjustment means comprises:

one end of said elasticized strap being fixedly attached to one end of said magnet-carrying means;

a ring flexibly secured to the opposite end of said magnet-carrying means for passage therethrough of said elasticized strap;

size-adjusting clip means mounted slidably on said elasticized strap, said strap passing through two parallel adjacent slots in said clip means, said strap extending through said ring and back to said clip means, the opposite end of said strap being rotatably secured to a clip means' slot-defining center post, whereby a secondary strap loop is formed between said clip means and said ring which, by movement of said clip means along said strap, and is adapted be enlarged to reduce the size of said elliptical opening in the magnetic therapeutic device to fit a smaller hand, and is adapted to be reduced to increase the size of said elliptcal opening in the magnetic therapeutic device to accommodate a larger hand.

* * * * *